(12) United States Patent
Minnigh et al.

(10) Patent No.: US 11,284,847 B2
(45) Date of Patent: Mar. 29, 2022

(54) X-RAY IMAGING SYSTEM AND METHOD

(71) Applicant: GE Precision Healthcare LLC, Wauwatosa, WI (US)

(72) Inventors: Todd Minnigh, Waukesha, WI (US); Timothy A Nustad, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 17 days.

(21) Appl. No.: 16/916,491

(22) Filed: Jun. 30, 2020

(65) Prior Publication Data

US 2021/0401384 A1 Dec. 30, 2021

(51) Int. Cl.
*A61B 6/00* (2006.01)
*G01N 23/04* (2018.01)

(52) U.S. Cl.
CPC ............ *A61B 6/4035* (2013.01); *A61B 6/488* (2013.01); *A61B 6/5205* (2013.01); *G01N 23/04* (2013.01)

(58) Field of Classification Search
CPC ..... A61B 6/4035; A61B 6/5205; A61B 6/488; G01N 23/04
See application file for complete search history.

(56) References Cited

U.S. PATENT DOCUMENTS

| | | | |
|---|---|---|---|
| 3,248,547 | A | 4/1966 | Van De Geijn |
| 4,868,857 | A | 9/1989 | Dobbins, III |
| 4,972,458 | A | 11/1990 | Plewes |
| 7,209,547 | B2 | 4/2007 | Baier |
| 7,929,661 | B2 | 4/2011 | Borghese |
| 2002/0186817 | A1* | 12/2002 | Schukalski ............. G21K 1/04 378/156 |
| 2014/0112441 | A1* | 4/2014 | Becker ................ A61B 6/4035 378/62 |
| 2017/0100089 | A1 | 4/2017 | Chang |
| 2020/0100758 | A1 | 4/2020 | Viswanathan |

OTHER PUBLICATIONS

Website: https://radiologykey.com/compensating-filters/ date: 2017.

* cited by examiner

*Primary Examiner* — Courtney D Thomas (57) ABSTRACT

A system for imaging includes an X-ray source for transmitting X-rays through a subject and a measurement sensor to acquire measurement data related to the subject. A detector is provided in the system to receive the X-ray energy of the X-rays after having passed through the subject. The system further includes a controller that receives the measurement data from the measurement sensor and processes the measurement data using an image processing algorithm to determine varying thickness of the subject at a plurality of locations within an area of interest. The controller further positions a filter between the X-ray source and the subject based on varying thickness of the subject and generates the image of the subject based on the detected X-ray energy at the X-ray detector.

21 Claims, 9 Drawing Sheets

X-RAY IMAGING SYSTEM AND METHOD

BACKGROUND

The subject matter disclosed herein relates to X-ray imaging system and method and specifically to modulation of the radiation field in the X-ray imaging system.

X-ray imaging has long been an accepted medical diagnostic tool. X-ray imaging systems are commonly used to capture, as examples, thoracic, cervical, spinal, cranial, and abdominal images that often include information necessary for a doctor to make an accurate diagnosis. X-ray imaging systems typically include an X-ray source and an X-ray detector. When having a thoracic X-ray image taken, for example, a patient stands with his or her chest against the X-ray detector as an X-ray technologist positions the X-ray detector and the X-ray source at an appropriate height. X-rays or the X radiations produced by the source travel through the patient's chest, and the X-ray detector then detects the X-ray energy generated by the source and attenuated to various degrees by different parts of the body. An associated control system obtains the detected x-ray energy from the X-ray detector and prepares a corresponding diagnostic image on a display.

In a conventional X-ray imaging system, the X-ray imaging is done with a near homogeneous radiation field. In other words, except for the anode heal effect, the X-ray flux is consistent across patient body that is exposed to the X-ray source field of view. During the exposure, the difference of body part thickness produces a subject contrast which exceeds the dynamic range of the detector. This results in an image which is either overexposed over the thinner areas of body or under exposed in the thicker areas. Even otherwise, one area of the patient body is under exposed and the complimentary area is over exposed to X-ray flux which is not desirable.

Therefore, there is a need for an improved X-ray imaging system and method.

BRIEF DESCRIPTION

In accordance with an embodiment of the present technique, a system for imaging is provided. The system includes an X-ray source operative to transmit X-rays through a subject and a measurement sensor for acquiring measurement data related to the subject. The system further includes a detector operative to receive the X-ray energy of the X-rays after having passed through the subject. The system also includes a controller for receiving the measurement data from the measurement sensor and for processing the measurement data using an image processing algorithm to determine varying thickness of the subject at a plurality of locations within an area of interest. The controller further positions a filter between the X-ray source and the subject based on varying thickness of the subject and generates the image of the subject based on the detected X-ray energy at the X-ray detector.

In accordance with another embodiment of the present technique, a method for imaging is provided. The method includes transmitting X-rays from an X-ray source to a subject and acquiring measurement data related to the subject. The method further includes processing the measurement data using an image processing algorithm to determine varying thickness of the subject at a plurality of locations within an area of interest and positioning a filter between the X-ray source and the subject based on varying thickness of the subject. The method also includes receiving the X-ray energy of the X-rays after having passed through the filter and the subject and generating the image of the subject based on the detected X-ray energy.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. Furthermore, the terms "circuit" and "circuitry" and "controller" may include either a single component or a plurality of components, which are either active and/or passive and are connected or otherwise coupled together to provide the described function.

The present approach addresses certain problems associated with image quality and/or radiation modulation in an X-ray imaging context. In general, in a conventional X-ray imaging system, the X-ray flux is consistent across patient body that is exposed to the X-ray source field of view. During the exposure, the difference of body part thickness produces a subject contrast which exceeds the dynamic range of the detector. This results in an image which is either overexposed over the thinner areas of body or under exposed in the thicker areas. The approach herein uses a sensor to identify the patient position and based on the patient position, precisely places a filter into the X-ray beam. This filter then attenuates the X-ray beam over thinner areas of body, while allowing larger amounts of radiation to be incident on thicker parts of the body. Thus, with this approach, the radiation pattern matches with the body part thickness.

Figure 1:
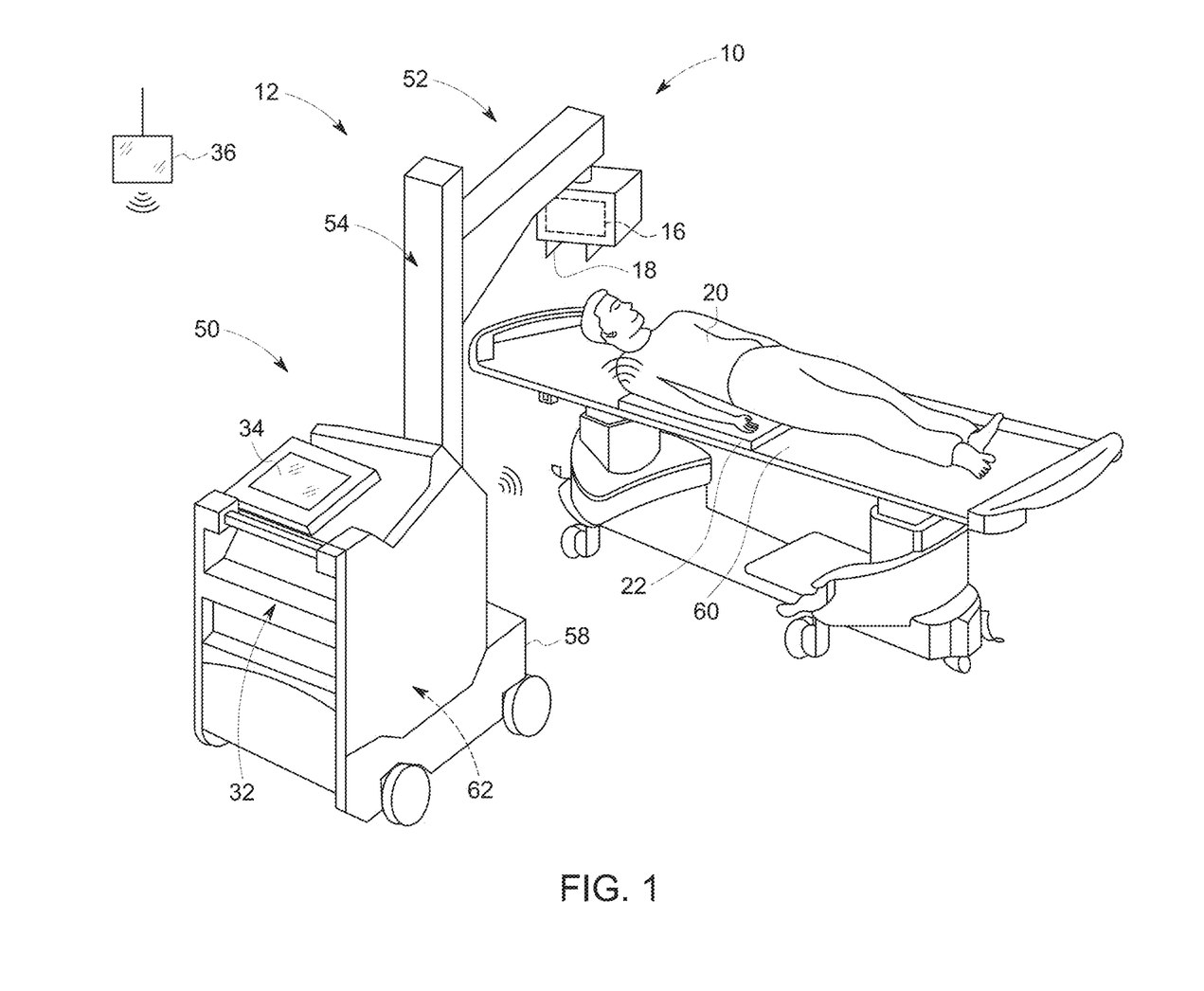
FIG. 1 is perspective view of an embodiment of a mobile X-ray system, equipped in accordance with aspects of the present approach.

With the preceding discussion of the present approach in mind, FIG. 1 depicts an imaging system that may be suitable for implementation of the present approach. In particular, an X-ray system is represented and referenced generally by reference numeral 10. In the illustrated embodiment, the X-ray system 10 is a digital X-ray system. The depicted X-ray system 10 is designed both to acquire original image data and to process image data for display in accordance with present techniques. The X-ray system 10 may be a radiographic imaging system used to collect a standalone image, a fluoroscopic imaging system used to collect multiple frames of real-time image data, a tomographic imaging system configured to image a patient region from multiple angles so as to generate a three-dimensional representation, or another suitable type of X-ray based imaging system.

In the embodiment illustrated in FIG. 1, the X-ray system 10 is a mobile imaging system 12 that may be moved to a patient recovery room, an emergency room, a surgical room, a neonatal ward, or any other space to enable imaging of a subject/patient 20 without transporting the subject 20 to a dedicated (i.e., fixed) X-ray imaging room. However, it should be appreciated that aspects of the present approach may also be used in fixed X-ray system environments. In the depicted example, the X-ray system 10 includes a mobile imager or mobile X-ray base station 50 and a portable digital X-ray detector 22 that is freely positionable with respect to the base station 50. In the depicted example, an X-ray base station 50 of the mobile imaging system 12 has a wheeled base 58 to facilitate movement of the station 50.

In the depicted example, a support arm 52 is provided in conjunction with a support column 54 to facilitate positioning of a radiation source 16 and collimator 18 with respect to the subject 20. By way of example, one or both of the support arm 52 and support column 54 may be configured to allow rotation of the radiation source 16 about one or more axes. However, in other examples as discussed herein, the structural and geometric components related to positioning of the X-ray source 16 may vary and/or may provide a different range of configurable motion and orientation of the X-ray source 16. The X-ray source 16 may be provided as an X-ray tube and may be provided in conjunction with a collimator 18 that helps shape or limit the X-ray beam incident on the subject 20.

In a mobile imaging context, as discussed herein, the subject 20 may be located on a bed 60 (or gurney, table or any other support) between the X-ray source 16 and the portable detector 22 and subjected to X-rays that pass through the subject 20. During an imaging sequence, the detector 22 receives X-rays that pass through the subject 20 and transmits imaging data to the base station 50. The portable detector 22 in this example is in wireless communication with the base unit 50, though in other examples communication may be completely or partially via a tethered (i.e., cable) connection. The base station 50 houses electronic circuitry 62 that acquires readout signals from the detector 22 and that may be processed to generate diagnostically useful images. In addition, the electronic circuitry 62 may provide and/or control power to one or both of the X-ray source 16 (i.e., controlling activation and operation of the source 16) and the wheeled base 58 (i.e., a movement system). In the depicted example, the base station 50 also has an operator workstation 32 and display 34 that facilitates user operation of the X-ray system 10. The operator workstation 32 may include a user interface to facilitate operation of the X-ray source 16 and detector 22. In one embodiment, the workstation 32 may be configured to function communicate on or through a network 36 of the medical facility, such as HIS, RIS, and/or PACS. In certain embodiments, the workstation 32 and/or detector 22 may wirelessly communicate with the network 36 wherein data transfer and data processing occur. It should also be noted that although, the technique herein is presented with respect to a mobile X-ray imaging system, the present technique may also be employed in fixed X-ray imaging system.

Figure 2:
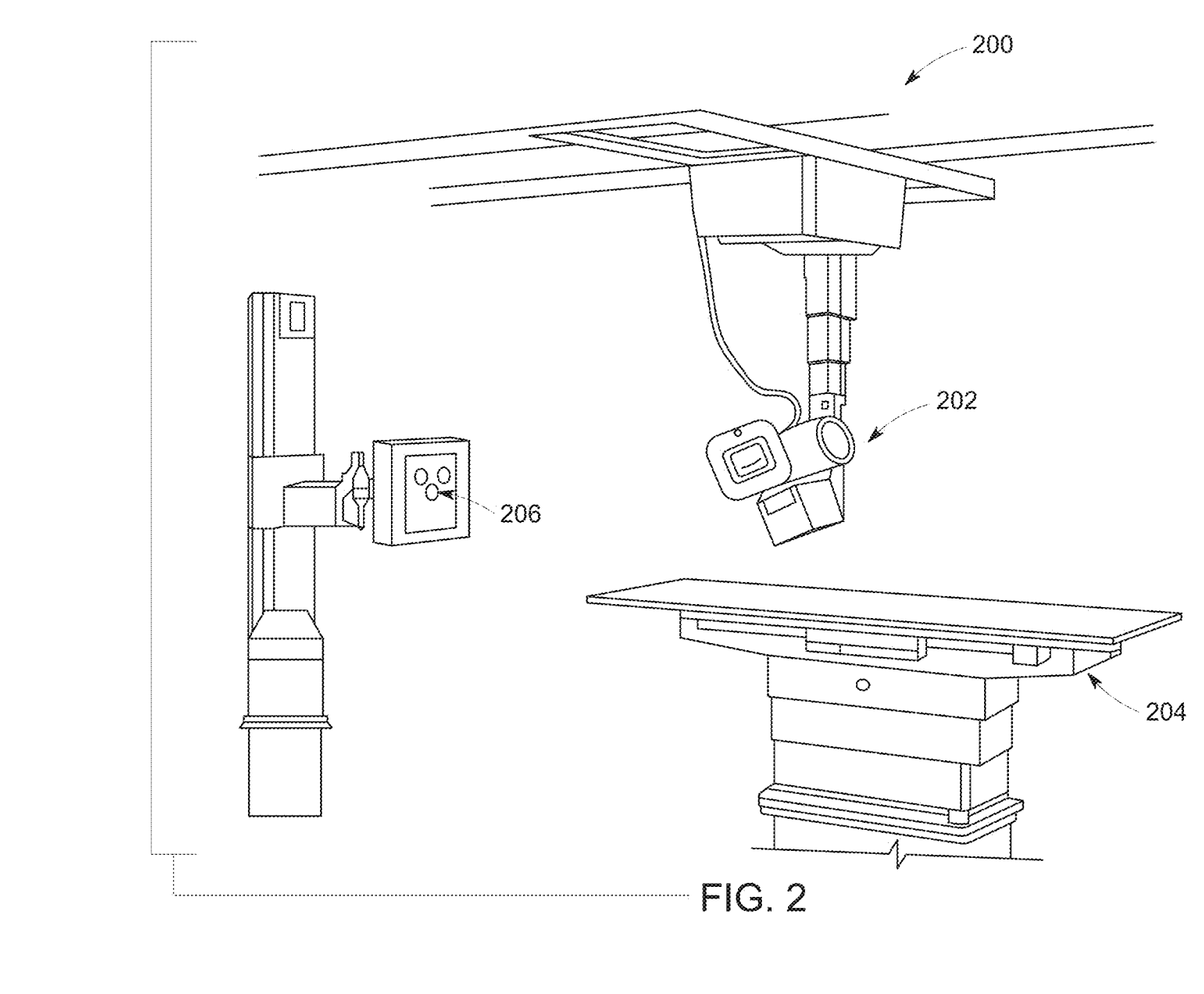
FIG. 2 is perspective view of an embodiment of a fixed X-ray system, equipped in accordance with aspects of the present approach.

FIG. 2 shows a fixed X-ray imaging system 200. The X-ray imaging system 200 includes an X-ray source 202 that is fixed but moves on wall railings. The X-ray imaging system further includes an X-ray table 204 where the patient lies and the X-ray source 202 radiates the body of the patient that is of interest. Within the X-ray table, X-ray detectors are located which adjustable and can slide in or out of the table 204. X-ray detectors detect the radiation from the X-ray source 202. A wall mounted X-ray detector 206 may also be used in the X-ray imaging system 200. A patient generally stands in front of the detector 206 and then the X-ray source 202 is focused on the patient body.

Figure 3:
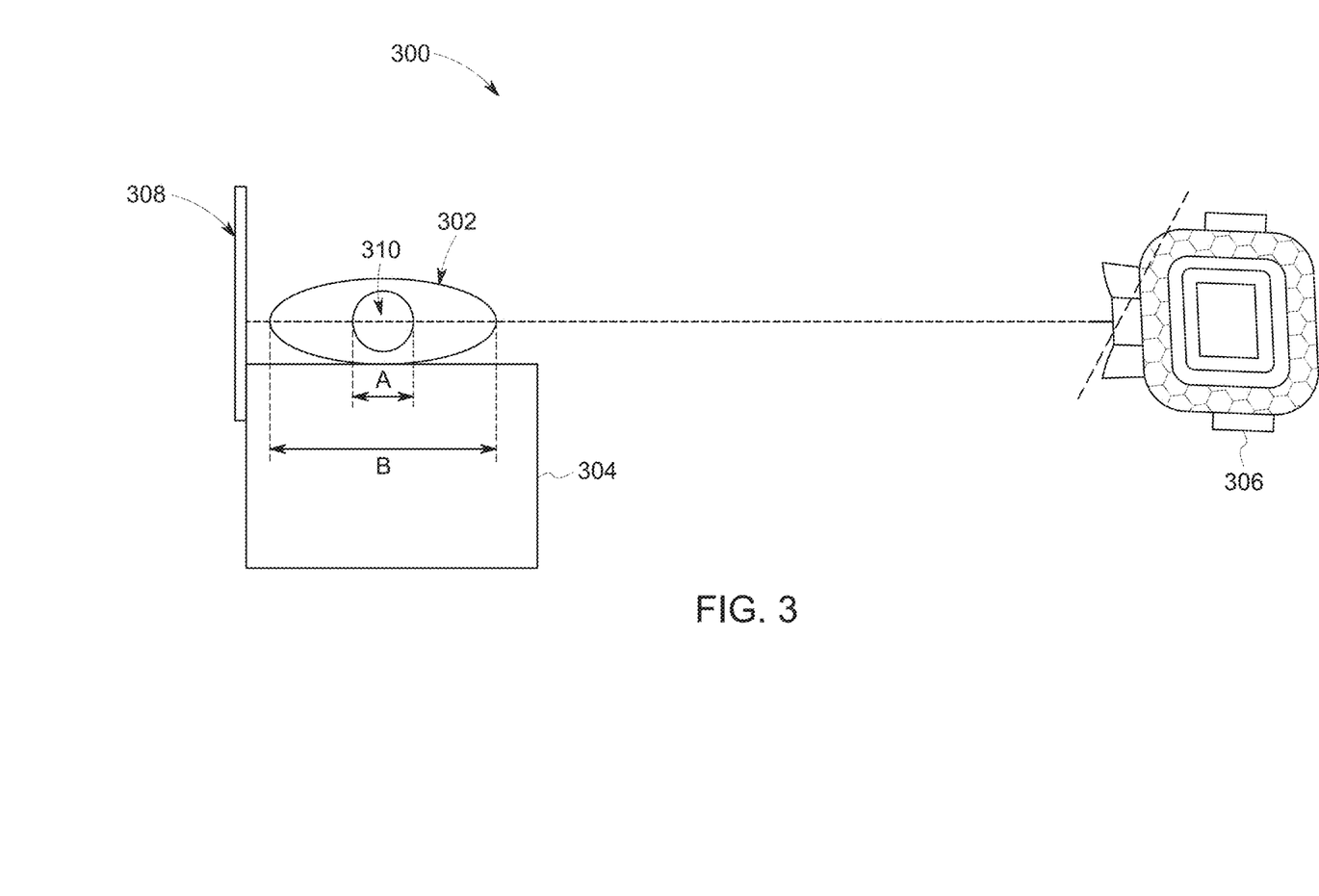
FIG. 3 is another view of an X-ray imaging system.

FIG. 3 shows an X-ray imaging system 300. As can be seen from FIG. 3, a subject/patient 302 is lying on an imaging table 304. Further, an X-ray tube 306 is being focused on the patient body and the radiation generated by the X-ray tube 306 is being detected by an X-ray detector 308. As can be seen, the thickness of the patient body varies from one point to another. For example, the area "A" (e.g., patient head 310) thickness is smaller than the area "B" (e.g., body area between two shoulders) thickness of the patient. In the embodiment shown, the patient body receives a roughly uniform radiation field from X-ray tube 306. In other words, the head 310 of the patient would receive the same amount of radiation as that of chest which is placed between two shoulders. Ideally area B would have a higher dose to accommodate for greater body part thickness. Moreover, the ratio of thicknesses A:B leads to high overall subject contrast that does not contribute to diagnostic information and may obscure required anatomy.

Figure 4:
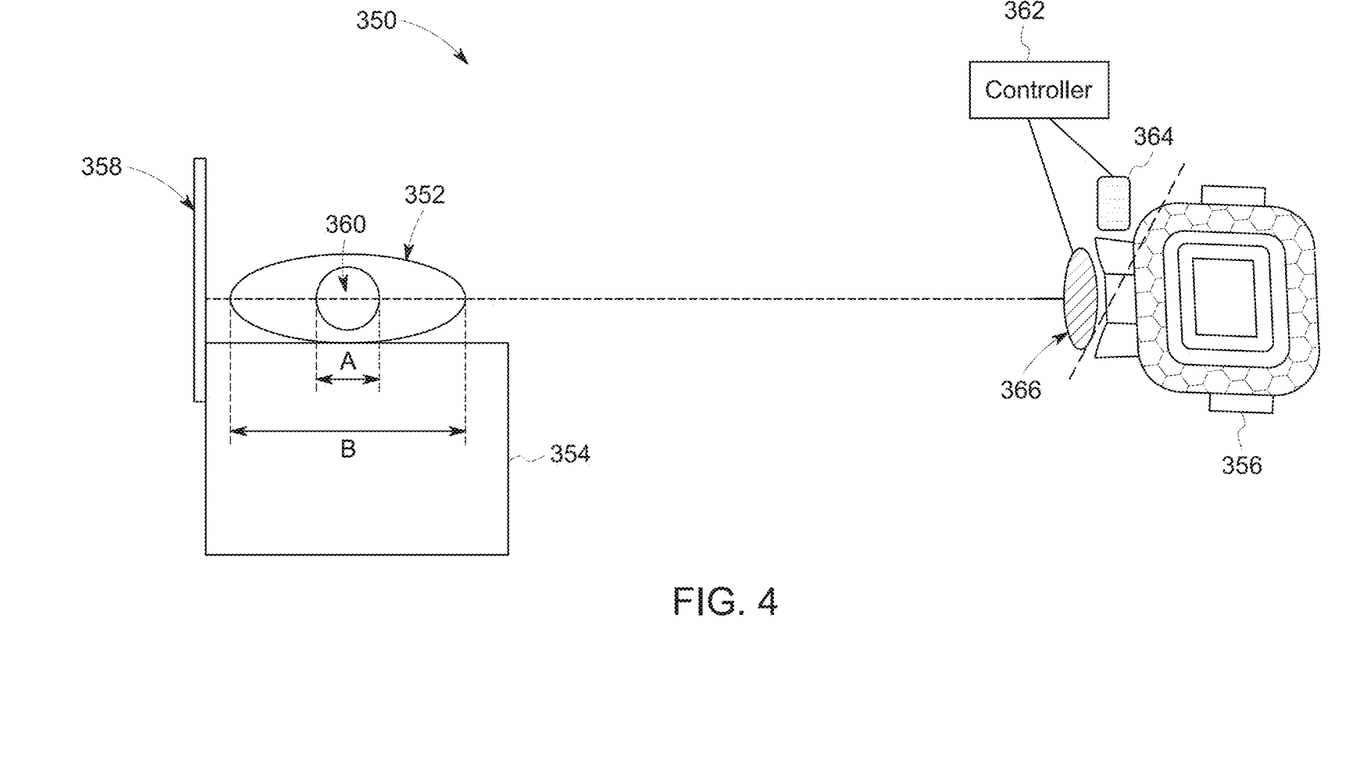
FIG. 4 is an X-ray imaging system, in accordance with an embodiment of the present technique.

FIG. 4 shows an X-ray imaging system 350, in accordance with an embodiment of the present technique. As can be seen, a subject/patient 352 is lying on an imaging table 354. Further, an X-ray tube 356 is being focused on the patient body and the radiation generated by the X-ray tube 356 is being detected by an X-ray detector 358. A sensor 364 is mounted on top of the X-ray tube 356 which captures measurement data of the patient body and provides the measurement data to a controller 362. In one embodiment, the sensor 364 may be a camera. In another embodiment, the sensor 364 is capable of stereovision and generates corresponding stereoscopic visual data that provides the distance of the patient body from the sensor 364. In yet another embodiment, sensor 364

Controller 362 then processes the measurement data provided by the sensor 364 and determines the precise position of the patient and thickness of the body parts of the patient using image processing algorithms. The image processing algorithms may include grey scale optimization algorithm, edge detection algorithm, filtering algorithm, and/or machine learning algorithm, for example. It should be noted that, the controller may be one or more computer processors, microcontrollers, or other logic-based devices that perform operations based on one or more sets of instructions (e.g., software).

In one embodiment, sensor 364 may include an ultrasound sensor. As will be appreciated by those skilled in the art, the ultrasound sensor transmits ultrasound waves usually emitted by a piezoelectric cell or electromagnetic acoustic (EMAT) sensor to the patient body. In this embodiment, based on the time taken by the ultrasound wave to return to the sensor, thickness of the patient body may be determined.

In yet another embodiment, the measurement data provided by sensor 364 may include a pre-shot/pre-exposure, which, as used herein, means an image of the subject 352 acquired by the x-ray source 356 and the detector 358 and analyzed prior to the system 350 acquiring subsequent projection/images of the subject 352. For example, in an embodiment, the pre-shot may be a low resolution two-dimensional ("2D") image acquired via a lower x-ray dose than images which are subsequently acquired via the x-ray source 356 and detector 358 and used to make a medical diagnosis. Additionally, the pre-shot may include multiple views of the subject 352.

Further, an X-ray filter 366 is placed in front of the X-ray beam path of the X-ray tube 356. X-ray filter 366 is selected by the controller 362 among a plurality of filters based on the position of the subject and thickness of the body parts of the subject determined by the controller 362. In general, each of the plurality of filters has a different attenuation pattern that is designed according to the subject thickness. Controller 362 also determines the position of the filter 366 in front of the X-ray tube 356. For example, in FIG. 4, if the operator is interested in taking an X-ray of the chest of the patient (i.e., an area of interest) then this information will be fed to the controller 362 through a user interface. Based on the image of the patient body provided by the sensor to the controller 362, controller 362 determines the varying thickness of the subject at a plurality of locations within the area of interest. As can be seen, the thickness of the patient body varies from one point to another. For example, the area "A" (e.g., subject head 360) thickness is smaller than the area "B" (e.g., body area between two shoulders) thickness of the subject. Accordingly, after the subject body thickness is determined by the controller 362, X-ray filter 366 is positioned in front of the X-ray tube 356 automatically. In the embodiment shown, the selected X-ray filter 366, provides more radiation to area B as compared to area A because the thickness of area B is more than the thickness of area A. This technique ensure that area B would have a higher dose of radiation to accommodate for greater body part thickness resulting in a good image quality and reduced exposure to body parts that are thin.

Figure 5:
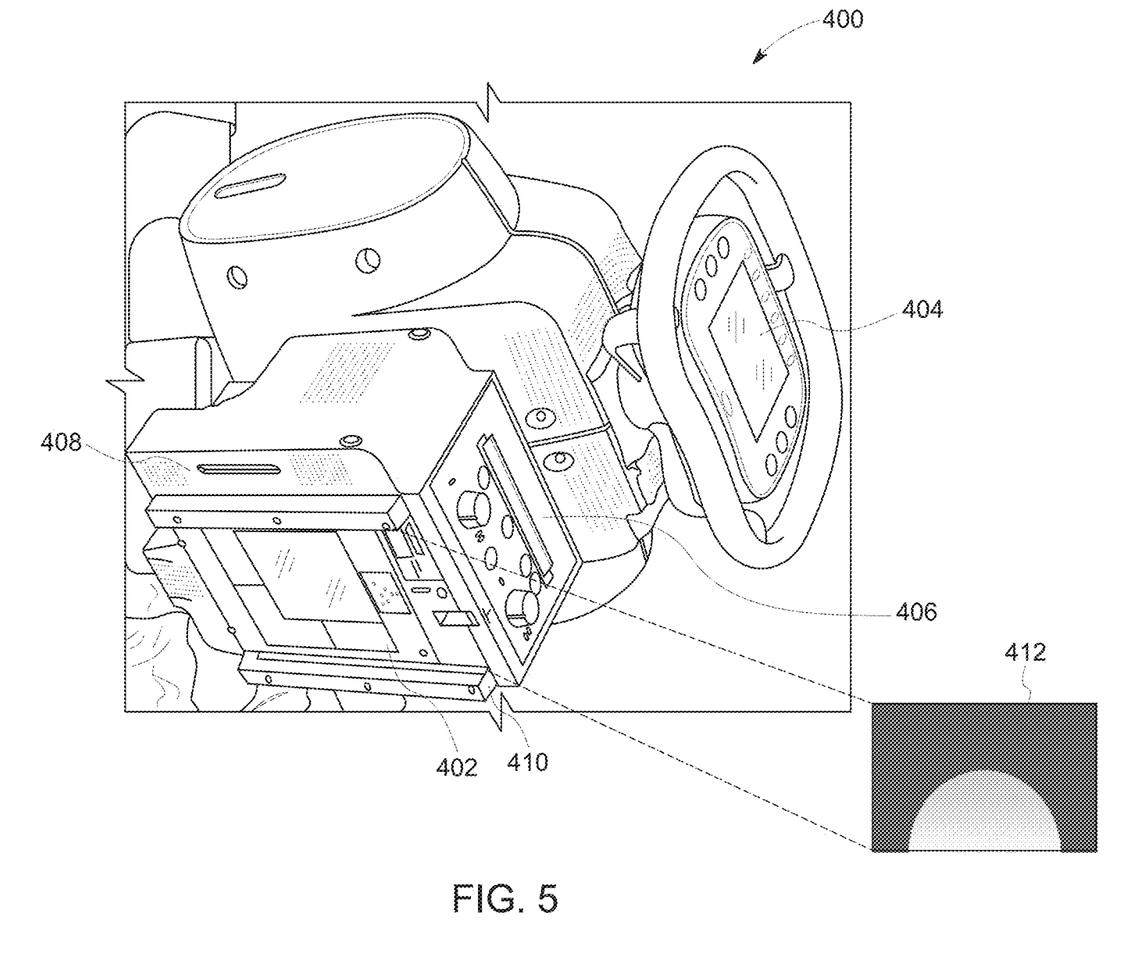
FIG. 5 is an X-ray source used in the X-ray imaging system of FIG. 4, in accordance with an embodiment of the present technique.

FIG. 5 illustrates details of an X-ray source 400, in accordance with an embodiment of the present technique. X-ray source 400 includes an X-ray tube 402, a display 404, and an input interface 406. An operator may use the input interface 406 to change the settings of the X-ray source 400. Moreover, the display 404 may display the settings of the X-ray source, for example. A measurement sensor 408 such as a camera is mounted on top of the X-ray tube 402 which captures measurement data corresponding to the subject body. It should be noted that the location of the measurement sensor 408 shown in FIG. 5 is just one example, and in other embodiments, the measurement sensor 408 may be located at other locations, for example, on the rod where the X-ray tube is located. Further, a filter slot 410 may be provided in front of the X-ray tube 402. The filter slot 410 is used to insert a filter 412 in front of the X-ray beam path of the X-ray tube 402. In one embodiment, filter slot 410 is provided inside the collimator and so the filters are provided near the collimator. When the filters are provided inside the collimator, filters may be of a round shape. In such an embodiment, a rotating disk having round filters may be provided inside the collimator which moves out of position when a homogeneous field is desired. The rotating disk may be controlled by an electric motor such as a stepper motor.

In one embodiment, the filter 412 may be of a sheet of material which changes effective energy of X-ray beams. The sheet of material may be formed from a material that changes attenuation pattern. For example, the sheet of material may be formed from lead, Aluminum, copper, plastic (e.g., acrylic), rare earth (e.g., erbium) or combinations thereof. The filters may be round, or polygon in shape depending on where they are placed.

Figure 6:
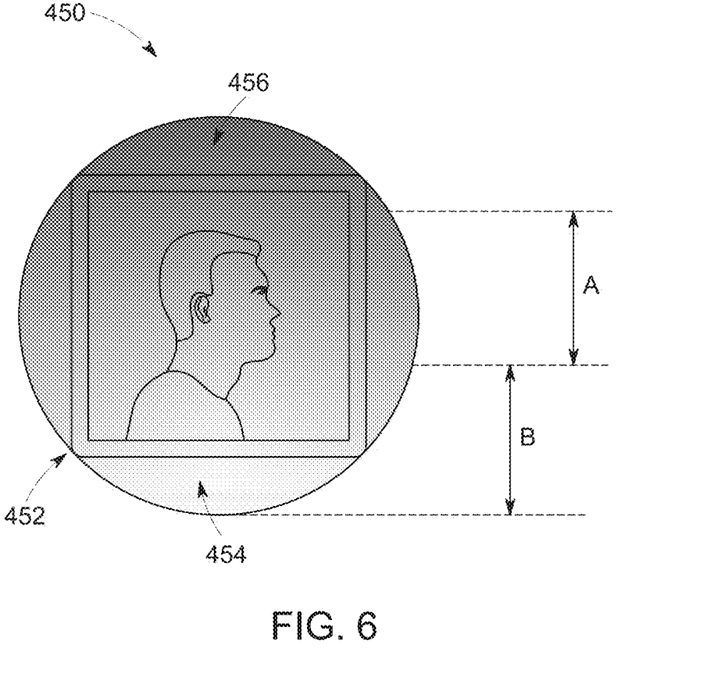
FIG. 6 is a pictorial diagram of a modulated radiation field focused on a subject, in accordance with an embodiment of the present technique.

FIG. 6 illustrates a pictorial diagram 450 of a modulated radiation field focused on a subject 452, in accordance with an embodiment of the present technique. As discussed above, the area A of the patient body (e.g., head) is thinner than area B (e.g., chest as seen from side view) of the patient body. Accordingly, a filter 452 is placed on the X-ray tube such that the exposure of the chest to the X-ray radiation is more as compared to the head. This effect is shown by the lighter area 454 of the filter 452 near the chest and the darker area 456 of the filter 452 near the head of the patient.

Figure 7:
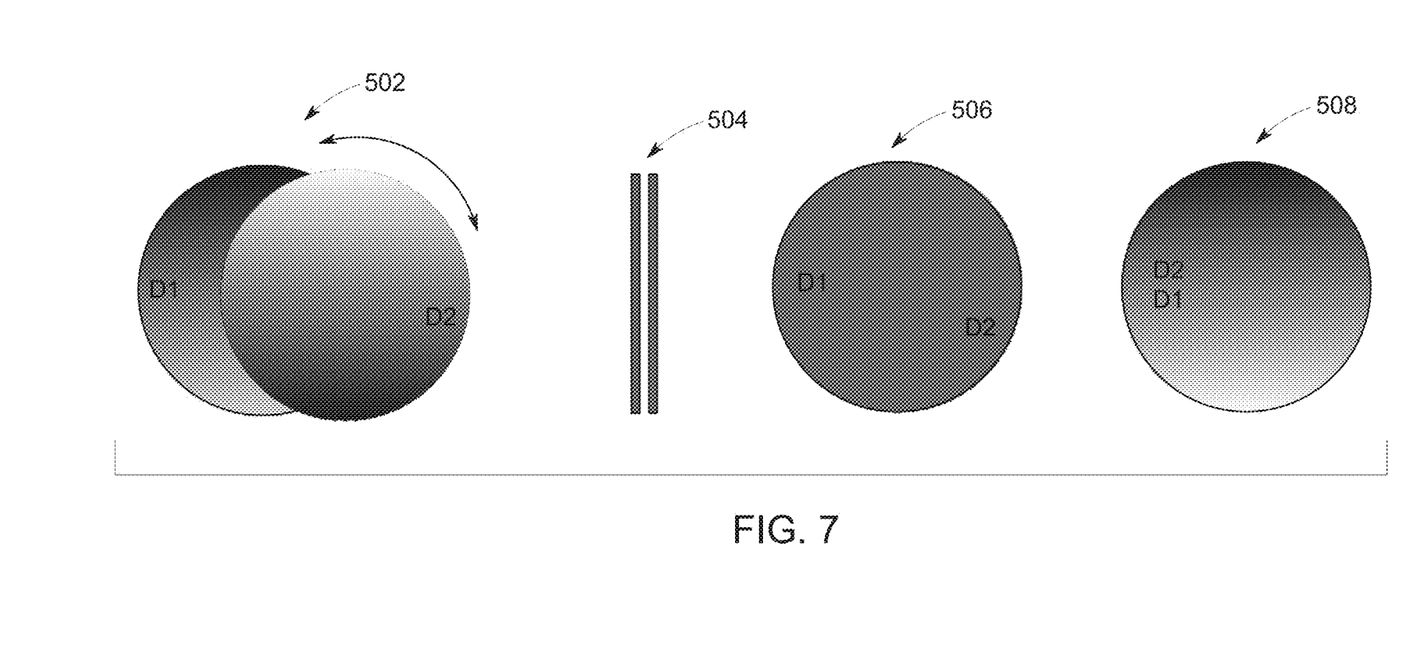
FIG. 7 depicts various views of a filter used in X-ray imaging system of FIG. 4, in accordance with an exemplary embodiment of the present disclosure.

FIG. 7 shows various views of a filter made up of a plurality of attenuating sheets or discs. Pictorial view 502 shows a front view of a filter made up of two discs D1 and D2 placed next to each other. The side view of the filter is shown in a pictorial view 504. As can be seen in pictorial view 504, the two discs D1 and D2 overlaid next to each other. It should be noted that selection of discs D1 and D2 is automatic and is determined by the processor of the imaging system based on the patient body thickness variation. Moreover, each of these discs D1 and D2 have different attenuation pattern and by rotating them in different steps in front of the X-ray tube, a radiation field produced by the X-ray tube may be modulated. The rotation steps of discs D1 and D2 are again determined by the processor depending on the radiation modulation requirements as per the patient body thickness variation. Pictorial views 506 and 508 show the effect of disc rotation e.g., in pictorial view 506, the discs D1 and D2 are overlapped such that X-ray radiation is almost blocked from transmitting to the patient body. Further, in pictorial view 508, the discs D1 and D2 are overlapped such that X-ray radiation is blocked from top portion of the filter but is allowed to pass through, through the bottom portion of the filter. In other words, in the embodiment shown, two round discs with complimentary radiopacity patterns could be rotated to create different radiation fields as needed. In yet another embodiment, a filter which dynamically changes radiopacity may also be used. Example of such a filter is a fluid-filled dynamic bowtie filter.

Figure 8:
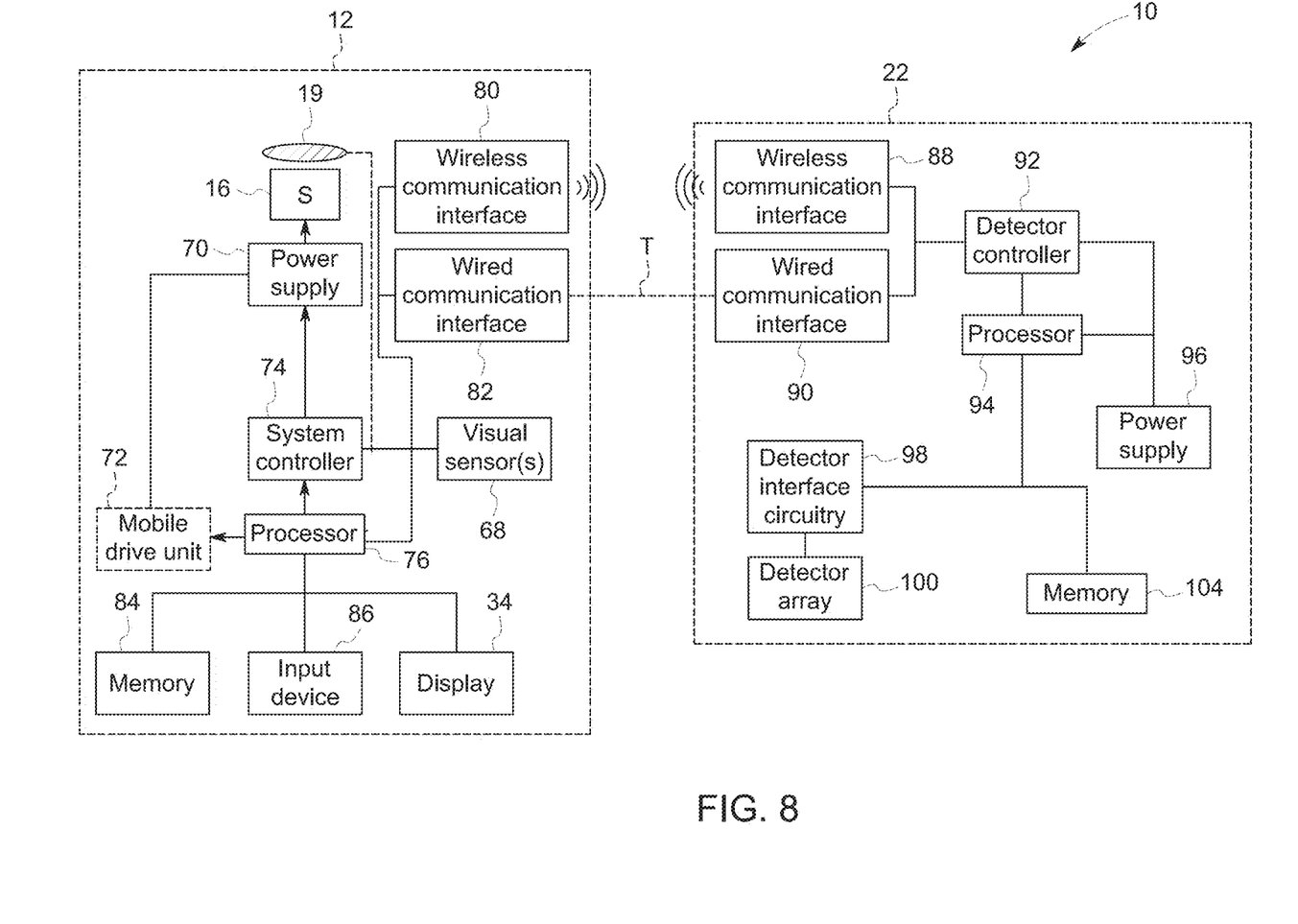
FIG. 8 is block diagram illustrates illustrating components of an imaging system and their interrelationship in accordance with an embodiment of the present technique.

FIG. 8 diagrammatically illustrates certain components of an imaging system and their interrelationship in accordance with an embodiment of the present technique. In the depicted example of FIG. 8, the imager system 12 includes the X-ray source 16 connected to a power supply 70 that furnishes both power and control signals for examination sequences. In addition, in mobile imaging systems the power supply 70 may furnish power to a mobile drive unit 72 of the wheeled base 58. The power supply 70 is responsive to signals from a system controller 74. In general, the system controller 74 commands operation of the imaging system to execute examination protocols and to process acquired image data. In the present context, the system controller 74 also includes signal processing circuitry, typically based upon a general purpose or application-specific circuitry, associated memory circuitry for storing programs and routines executed by the computer, as well as configuration parameters and image data, interface circuits, and so forth. The system controller 74 may include or may be responsive to a processor 76. The processor 76 receives image data from the detector 22 and processes the data to reconstruct an image of a subject.

Further, the controller 74 may generate, as discussed herein, a filter signal that is utilized to automatically position the filter 19 onto the X-ray source 16. In another embodiment, the filter signal may be utilized to automatically select a specific type of filter 19 among a plurality of filters depending on the radiation requirement. The selection of the filter or the position of the filter 19 is dependent on desired modulation of the X-ray radiation from the X-ray source 16. With this in mind, the controller 74, in accordance with the present approach may receive inputs from one or more sensor(s) 68 (e.g., cameras) of the imager system 12 to provide desired modulation of the X-ray radiation as will be explained below.

In the implementation shown, the processor 76 is linked to a wireless communication interface 80 that allows wireless communication with the detector 22, e.g., a portable detector. Further, the processor 76 may be linked to a wired communication interface 82 that allows communication with the detector 22 via a tether (e.g., a multi-conductor cable). The imager system 12 may also be in communication with a server. The processor 76 is also linked to a memory 84, an input device 86, and the display 34. The memory 84 stores configuration parameters, calibration files received from the detector 22, and lookup tables used for image data processing. The input device 86 may include a mouse, keyboard, or any other device for receiving user input, as well as to acquire images using the imager system 12. The display 34 allows visualization of output system parameters, images, and so forth.

The detector 22 includes a wireless communication interface 88 for wireless communication with the imager system 12, as well as a wired communication interface 90, for communicating with the detector 22 when it is tethered to the imager system 12. The detector 22 may also be in communication with a server. It is noted that the wireless communication interface 88 may utilize any suitable wireless communication protocol, such as an ultra wideband (UWB) communication standard, a Bluetooth communication standard, or an 802.11 communication standard, or any other suitable wireless communication standard. Moreover, the detector 22 is coupled or includes a detector controller 92 which coordinates the control of the various detector functions. For example, the detector controller 92 may execute various signal processing and filtration functions, such as for initial adjustment of dynamic ranges, interleaving of digital image data, and so forth. The detector controller 92 is responsive to signals from the system controller 74, as well as the detection circuitry 78. The detector controller 92 is linked to a processor 94 that in turn is linked to a memory 104. The processor 94, the detector controller 92, and all of the circuitry receive power from a power supply 96. The power supply 96 may include a battery. In some embodiments, the detector 22, including the power supply 96, may receive power from the power supply 70 when tethered to the imager system 12.

In the depicted example the processor 94 is linked to detector interface circuitry 98. In one embodiment, the detector 22, which may be used in radiographic, fluoroscopic, tomographic, or other imaging operations, converts X-ray photons incident on its surface to lower energy (e.g., optical light) photons. The detector 22 includes a detector array 100 that includes an array of photodetector elements that generate responsive electrical signals in response to the light photons generated in this manner such that the electrical signals are representative of the number of photons or the intensity of radiation impacting individual pixel regions of the detector surface. Alternatively, the detector 22 may convert the X-ray photons directly to electrical signals (i.e., a direct conversion type detection mechanism). These electrical signals are converted to digital values by the detector interface circuitry 98, which provides the values to the processor 94 to be converted to imaging data and sent to the imager system 12 to reconstruct an image of the features within a subject. Alternatively, the imaging data may be sent from the detector 22 to a server to process the imaging data.

With the preceding discussion of an imaging system 10 in mind, in accordance with the present approach a filter 19 is positioned with respect to a patient anatomy of interest and an X-ray emission source 16 of a mobile system X-ray imager 12, allowing a modulated radiation field. The filter 19 associated with the source 16 of X-ray emission may be adjusted automatically to modulate the X-ray beam incidence on the subject 20 based on a filter signal received from processor 76 as explained earlier.

Figure 9:
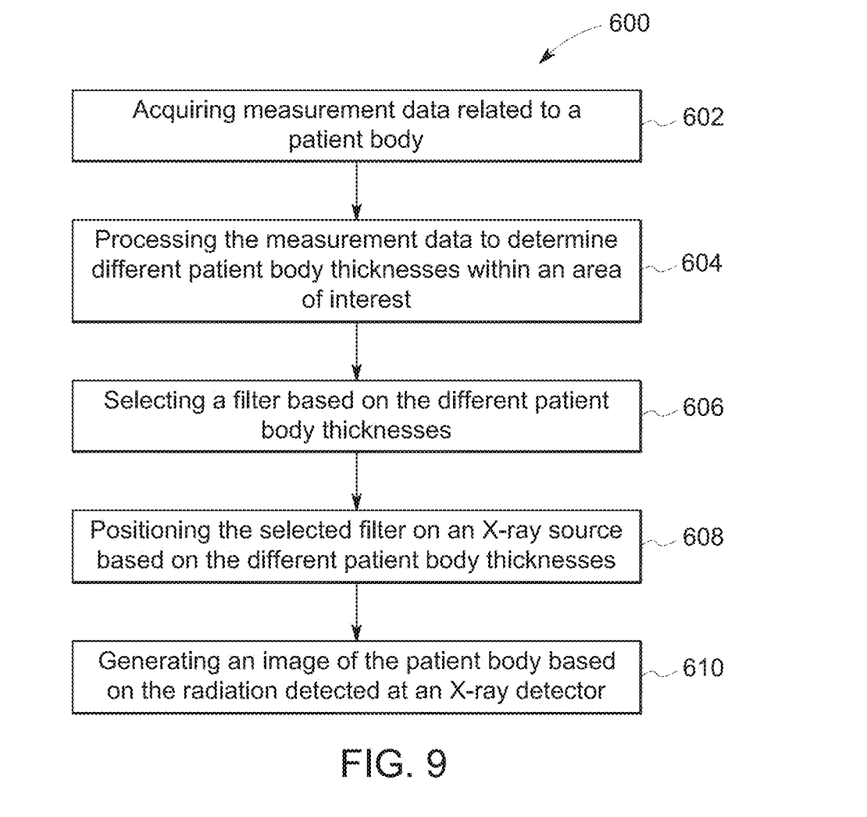
FIG. 9 is a flow chart depicting a method for imaging a subject in accordance with an embodiment of the present disclosure.

FIG. 9 is a block diagram 600 depicting a method for imaging a subject. The method includes acquiring measurement data related to a subject body at step 602. The measurement data may be acquired from a sensor such as a camera or an ultrasound sensor. In one embodiment, the measurement data may include a pre-shot/pre-exposure acquired by the imaging system. At step 604, the measurement data is processed by a processor using image processing algorithms to determine varying thickness of the subject at a plurality of locations within an area of interest. The area of interest is the body part on which the X-ray scan is being performed e.g., chest or spine. The image processing algorithms may include grey scale optimization algorithm, edge detection algorithm, filtering algorithm, and/or machine learning algorithm, for example.

At step 606, an X-ray filter is selected among a plurality of filters based on the thickness of the subject at a plurality of locations. Each of the plurality of filters has a different attenuation pattern that is designed according to the subject thickness and in step 608, the selected filter is positioned on an X-ray source depending on the subject thicknesses determined by the processor within the area of interest. The X-ray filter attenuates the X-ray beam from the X-ray source over thinner areas of body, while allowing larger amounts of radiation to be incident on thicker parts of the body. In one embodiment, the filter includes a sheet of material placed inside the collimator and which changes effective energy of X-ray beams. The sheet of material may be formed from a material that changes attenuation pattern. For example, the sheet of material may be formed from lead, Aluminum, copper, plastic (e.g., acrylic), rare earth (e.g., erbium) or combinations thereof. In another embodiment, the filter may be made up of a plurality of attenuating sheets placed next to each other. In one embodiment, each of the plurality of attenuating sheets may be moved with respect to each other to create different radiation fields as desired.

Finally, at step 610, an image of the subject body is generated based on the radiation detected at an X-ray detector. In general, the modulated radiation field from X-ray source is incident on the subject. The radiation field is attenuated to various degrees by different parts of the subject body and the attenuated radiation field is detected by the X-ray detector. An associated control system obtains the detected x-ray energy from the X-ray detector and prepares a corresponding diagnostic image on a display.

The advantages of the present technique include reduced radiation exposure to thinner body parts, ability to capture wider variety of subject thicknesses within one view and improved penetration through thicker body parts without overexposure of thinner parts. Further, the technique presented herein may be utilized in a plurality of X-ray applications such as Lateral cervical spine (C-spine), Lateral Lumbar spine (L-spine), Lateral Thoracic spine (T-spine) scan. Other applications may include posterioranterior (PA) chest, anteriorposterior (AP) chest, AP T-spine and AP ribs scan.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for imaging comprising:
   an X-ray source operative to transmit X-rays through a subject, wherein the X-ray source includes an X-ray tube and a collimator;
   a measurement sensor for acquiring measurement data related to the subject;
   a detector operative to receive the X-ray energy of the X-rays after having passed through the subject;
   a filter arrangement provided inside the collimator comprising a rotating disk having at least two round filters with complimentary radiopacity patterns; and
   a controller operative to:
      receive the measurement data from the measurement sensor;
      process the measurement data using an image processing algorithm to determine varying thickness of the subject at a plurality of locations within an area of interest;
      rotate the at least two round filters to create different radiation fields based on varying thickness of the subject;
      generate the image of the subject based on the detected X-ray energy at the X-ray detector.

2. The system of claim 1, wherein the measurement data includes a camera image of the subject, an ultrasound sensor output signal of the subject or a pre-shot/pre-exposure image of the subject.

3. The system of claim 2, wherein the image processing algorithm includes grey scale optimization algorithm, edge detection algorithm, filtering algorithm, or machine learning algorithm.

4. The system of claim 1, wherein the controller is operative to select the at least two round filters among a plurality of filters based on varying thickness of the subject at the plurality of locations.

5. The system of claim 1, wherein the controller is operative to position the at least two round filters such that the filter arrangement attenuates the X-rays from the X-ray source over thinner body area of subject, while allowing larger amounts of radiation to be incident on thicker body area of the subject.

6. The system of claim 5, wherein each of the two round filters includes a sheet of a material that changes effective energy of the X-rays.

7. The system of claim 6, wherein the material includes lead, aluminum, copper, plastic, rare earth or combinations thereof.

8. The system of claim 6, wherein the sheet of material is round or polygon in shape.

9. The system of claim 6, wherein each of the two round filters is operative to dynamically change radiopacity.

10. The system of claim 5, wherein each of the two round filters includes a plurality of sheets placed over one another and moved with respect to each other to modulate radiation from the X-ray source.

11. The system of claim 10, wherein the plurality of sheets is controlled by an electric motor.

12. The system of claim 1, wherein the area of interest is selected based on a type of X-ray scan being performed.

13. The system of claim 1, wherein the measurement data includes a pre-exposure image of the subject, wherein the pre-exposure image includes a low resolution two-dimensional ("2D") image acquired via a lower x-ray dose than images which are acquired to make a medical diagnosis.

14. A method for imaging comprising:
    transmitting X-rays from an X-ray source to a subject, wherein the X-ray source includes an X-ray tube and a collimator;
    acquiring measurement data related to the subject;
    processing the measurement data using an image processing algorithm to determine varying thickness of the subject at a plurality of locations within an area of interest;
    providing a filter arrangement inside the collimator comprising a rotating disk having at least two round filters with complimentary radiopacity patterns;
    rotating the at least two round filters to create different radiation fields based on varying thickness of the subject;
    receiving the X-ray energy of the X-rays after having passed through the filter arrangement and the subject; and
    generating the image of the subject based on the detected X-ray energy.

15. The method of claim 14, wherein the measurement data includes a camera image of the subject, an ultrasound sensor output signal of the subject or a pre-shot/pre-exposure image of the subject.

16. The method of claim 14, wherein each of the two round filters is selected among a plurality of filters based on varying thickness of the subject at the plurality of locations.

17. The method of claim 14, wherein each of the two round filters is positioned such that the filter attenuates the X-rays from the X-ray source over thinner body area of subject, while allowing larger amounts of radiation to be incident on thicker body area of the subject.

18. The method of claim 17, wherein each of the two round filters includes a plurality of sheets placed over one another and moved with respect to each other to modulate radiation from the X-ray source.

19. The method of claim 17, wherein each of the two round filters includes a sheet of a material that changes effective energy of the X-rays.

20. The method of claim 19, wherein the material includes lead, aluminum, copper, plastic, rare earth or combinations thereof.

21. The method of claim 19, wherein each of the two round filters dynamically changes radiopacity.

* * * * *